(12) United States Patent
Rice et al.

(10) Patent No.: US 10,955,275 B2
(45) Date of Patent: Mar. 23, 2021

(54) SYSTEMS AND METHODS FOR CALIBRATING AND CORRECTING A SPECKLE CONTRAST FLOWMETER

(71) Applicant: Covidien LP, Mansfield, MA (US)

(72) Inventors: Tyler Bywaters Rice, Irvine, CA (US); Sean Michael White, Irvine, CA (US); Bruce Yee Yang, Irvine, CA (US)

(73) Assignee: Covidien LP, Mansfield, MA (US)

( * ) Notice: Subject to any disclaimer, the term of this patent is extended or adjusted under 35 U.S.C. 154(b) by 201 days.

(21) Appl. No.: 16/093,597

(22) PCT Filed: Apr. 18, 2017

(86) PCT No.: PCT/US2017/028178
§ 371 (c)(1),
(2) Date: Oct. 12, 2018

(87) PCT Pub. No.: WO2017/184630
PCT Pub. Date: Oct. 26, 2017

(65) Prior Publication Data
US 2020/0158548 A1 May 21, 2020

Related U.S. Application Data

(60) Provisional application No. 62/324,903, filed on Apr. 20, 2016.

(51) Int. Cl.
*G01F 1/708* (2006.01)
*A61B 5/026* (2006.01)
(Continued)

(52) U.S. Cl.
CPC ......... *G01F 1/7086* (2013.01); *A61B 5/0261* (2013.01); *G01B 9/02094* (2013.01); *G01N 21/47* (2013.01); *G01N 2021/479* (2013.01)

(58) Field of Classification Search
CPC .... A61B 5/0261; G01F 1/7086; G01N 21/47; G01B 9/02094
See application file for complete search history.

(56) References Cited

U.S. PATENT DOCUMENTS

| | | |
|---|---|---|
| 4,109,647 A | 8/1978 | Stern et al. |
| 4,476,875 A | 10/1984 | Nilsson et al. |

(Continued)

FOREIGN PATENT DOCUMENTS

| | | |
|---|---|---|
| CN | 101156769 A | 4/2008 |
| CN | 101243966 A | 8/2008 |

(Continued)

OTHER PUBLICATIONS

First Office Action and Search Report, and translation thereof, from counterpart Chinese Application No. 201780024284.X, dated Apr. 15, 2020, 23 pp.

(Continued)

*Primary Examiner* — Robert J Hance
(74) *Attorney, Agent, or Firm* — Shumaker & Sieffert, P.A.

(57) ABSTRACT

Disclosed herein are systems, methods, and devices for calibrating contrast measurements from laser speckle imaging systems to accurately determine unknown particle motion characteristics, such as flow rate. The calibration stores to memory calibration data, which may include a set of measurements from samples with known particle characteristics and/or estimates of noise, including the effects on contrast arising from undesired signals unrelated to the unknown particle motion characteristics. The calibration data may be accessed and used to correct an empirical measurement of contrast and/or interpolate a value of the unknown particle motion characteristic. The system may include a light source, photodetector, processor, and memory, which can be combined into a single device, such (Continued)

as a wearable device, for providing calibrated flow measurements. The device may be used, for example, to measure blood flow, cardiac output, and heart rate, and can be used to amplify the pulsatile signal.

27 Claims, 9 Drawing Sheets

(51) Int. Cl.
*G01B 9/02* (2006.01)
*G01N 21/47* (2006.01)

(56) References Cited

U.S. PATENT DOCUMENTS

| | | | |
|---|---|---|---|
| 5,291,886 A | 3/1994 | Katayama et al. | |
| 2003/0183726 A1 | 8/2003 | Presura et al. | |
| 2010/0155577 A1 | 6/2010 | Kiesel et al. | |
| 2011/0013002 A1 | 1/2011 | Thompson et al. | |
| 2011/0137140 A1* | 6/2011 | Tearney | A61B 5/0066 600/310 |
| 2012/0095354 A1* | 4/2012 | Dunn | A61B 5/0261 600/504 |
| 2012/0162438 A1 | 6/2012 | Thakor et al. | |
| 2013/0296715 A1 | 11/2013 | Lasser et al. | |
| 2014/0049779 A1* | 2/2014 | Tin | G01B 11/303 356/456 |
| 2015/0182136 A1* | 7/2015 | Durduran | A61B 5/0073 600/425 |
| 2016/0066790 A1* | 3/2016 | Shcherbakov | A61B 5/0062 356/511 |
| 2017/0023667 A1 | 1/2017 | Angelsen et al. | |

FOREIGN PATENT DOCUMENTS

| | | | | |
|---|---|---|---|---|
| CN | 101485565 A | 7/2009 | | |
| CN | 103330557 A | 10/2013 | | |
| CN | 104125801 A | 10/2014 | | |
| CN | 104523225 A | 4/2015 | | |
| WO | WO-2016025438 A1 * | 2/2016 | | A61B 5/002 |

OTHER PUBLICATIONS

Examination Report from counterpart European Application No. 17786485.7, dated Jun. 26, 2020, 6 pp.

Luo et al., "Optical coherence Doppler tomography quantifies laser speckle contrast imaging for blood flow imaging in the rat cerebral cortex," Optical Society of America, vol. 33, No. 10, XP001514625, May 15, 2008, 3 pp.

Ringuette, "Application of Vertical-cavity Surface-emitting Lasers for Simultaneous Laser Speckle Contrast and Intrinsic Optical Signal Imaging: Toward Chronic Portable Cortical Hemodynamic Imaging", Thesis for the Institute of Biomaterials and Biomedical Engineering, University of Toronto, XP055514906, Jun. 1, 2012, retrieved from https:i/tspace. library.utoronto.calbitstream/1847/132620/3/Ringuette_Dene_AA_201206_MASc_thesis.pdf, 258 pp.

International Preliminary Report on Patentability from International Application No. PCT/US2017/028178, dated Oct. 23, 2018, 11 pp.

Communication Pursuant to Rules 161(1) and 162 EPC dated Nov. 27, 2018 from counterpart European Application No. 17786485.7, 3 pp.

Briers, "Laser Doppler, speckle and related techniques for blood perfusion mapping and imaging," Institute of Physics Publishing, Physiological Measurement, vol. 22, R35, Oct. 29, 2001, 35 pp.

Briers et al., "Laser speckle contrast analysis (LASCA): a nonscanning, full-field technique for monitoring capillary blood flow," Research Papers, Journal of Biomedical Optics, vol. 1, Issue 2, Apr. 1996, pp. 174-179.

Boas et al., "Laser speckle contrast imaging in biomedical optics," Journal of Biomedical Optics, vol. 15, Issue, 1, Jan./Feb. 2010, 12 pp.

Zakharov et al., "Quantitative modeling of laser speckle imaging," Optical Society of America, Opt. Lett. 31, Jul. 28, 2006, pp. 3465-3467.

Skipetrov et al., "Noise in laser speckle correlation and imaging techniques," University of Zurich, Optics Express, vol. 18, Issue 14, Jul. 5, 2010, pp. 14519-14534.

Draijer, Matthijs et al., "Twente Optical Perfusion Camera: system overview and performance for video rate laser Doppler perfusion imaging", Optics Express, vol. 17, No. 5, Mar. 2, 2009, p. 3211, XP055427566, US; ISSN: 2161-2072, DOI: 10.1364/OE.17.003211.

Extended European Search Report for PCT/US2017028178, dated Nov. 10, 2019 in 10 pages.

Ren, Hugang et al., "Multichannel optical brain imaging to separate cerebral vascular, tissue metabolic, and neuronal effects of cocaine", Photonic Therapeutics and Diagnostics VIII, SPIE, No. 1, Feb. 3, 2012, pp. 1-8, XP060022653, DOI: 10.1117/12.910160 [retrieved on Jan. 1, 1901].

Ren, Wenqi et al., "Quasi-simultaneous multimodal imaging of cutaneous tissue oxygenation and perfusion", Journal of Biomedical Optics, vol. 20, No. 12, Sep. 10, 2015, p. 121307, XP055585473.

Yuan, Shuai et al., "Calibration in laser speckle contrast imaging", Biomedical Optics, Jan. 1, 2006, p. ME32, XP55627821, DOI: 10.1364/BIO.2006.ME32.

International Search Report for PCT Application No. PCT/US17/28178, dated Jul. 13, 2017, in 2 pages.

* cited by examiner

SYSTEMS AND METHODS FOR CALIBRATING AND CORRECTING A SPECKLE CONTRAST FLOWMETER

INCORPORATION BY REFERENCE

This application is a U.S. national stage application of International Patent Application No. PCT/US2017/028178, filed Apr. 18, 2017, which claims priority benefit of U.S. Provisional Patent Application No. 62/234,903, filed Apr. 20, 2016, which are is incorporated herein by reference in their entirety for all purposes. Any and all applications related thereto by way of priority thereto or therefrom are hereby incorporated by reference in their entirety.

BACKGROUND

This disclosure relates to devices, systems and methods for calibrating and correcting flowmetry measurements made using laser speckle imaging (LSI). LSI is an optical technique for determining the rate of motion within a sample using interferometric information. LSI is typically performed with a coherent illumination source and image sensor, where light interrogates a sample and randomly interferes on the image sensor, producing a signature "speckle" pattern. The pattern is then analyzed, in space and/or in time, to determine particle motion within the sample.

Dynamic Light Scattering (DLS) is a technique for determining particle size and fluid flow rate that utilizes coherent illumination and interference. The technology has been used in medical applications for some time to measure blood perfusion [1]. In recent years, DLS technologies have seen major innovation and are now performed in a variety of ways [2]. One DLS method, called laser speckle imaging (LSI), uses a coherent laser source to illuminate a sample of light scattering particles, and images the scattered light using a multi-pixel detector. Early iterations used multiple photodetectors [3, 4], but many instruments now use a silicon-based camera sensor [5]. The sensor records the so-called "speckle" pattern, produced by light interference, as the scattered coherent light recombines onto the detection element. If the scattering particles are in motion, the interference pattern will fluctuate over time. The detection element has a finite exposure time, and if the interference pattern fluctuates during the exposure, the speckles will "blur," or their light intensity will be averaged within the detection element pixels. Researchers have previously developed a methodology to quantify the amount of "blurring" during the exposure by analyzing the amount of contrast between pixel intensity values in time and/or space. One common way to quantify contrast is to calculate the standard deviation of a local neighborhood of pixel intensities, often normalizing to the mean [6]. This parameter is typically referred to as the "speckle contrast." A reduction in speckle contrast indicates an increase in flow and vice versa. The speckle contrast may alternatively be calculated for multiple frames in time.

LSI is a useful technology in biomedical research to study blood flow within vascularized tissue [7]. Cells and other structures within the blood scatter the coherent light as they flow through the vasculature, and LSI can quantify this flow. Further developments have seen the inclusion of Monte Carlo simulation results and static scattering components in the LSI model [8]. However, a major disadvantage to LSI is that it is highly susceptible to numerous sources of noise. Because LSI relies on the standard deviation between pixels, noise from random and/or system sources, such as shot noise or dark sensor noise, can affect the speckle contrast and hence impact the quantification of flow. A myriad of other factors may affect the formulation of the speckle pattern onto the sensor including: coherence length of the laser (which varies between lasers and manufacturers), numerical aperture of the optical system, pixel size, wavelength, and ambient light, among others [9].

SUMMARY

LSI is an optical technique for determining the rate of motion within a sample using interferometric information. LSI is typically performed with a coherent illumination source and image sensor, where light interrogates a sample and randomly interferes on the image sensor, producing a signature "speckle" pattern. The pattern is then analyzed, in space and/or in time, to determine particle motion within the sample. Particularly, this disclosure relates to ways to correct errors in the output given by laser speckle contrast analysis. Errors may arise when undesired signals affect the speckle contrast. Generally these signals are unrelated to particle motion characteristics of the light scattering particles in the interrogated sample. The effect of the undesired signals on the speckle contrast value may be determined through calibration steps involving measurements of known samples (samples with known particle characteristics), or the effect may be estimated from known characteristics of the sensor, source, or other conditions. The correction may account for and reduce or eliminate the errors caused by non-flow elements that affect speckle contrast such as, but not limited to: sensor noise, source coherence (due to fluctuations in laser power supply voltage), statistical variance (natural variation in speckle pattern statistics), and ambient light. More specifically, in a particular non-limiting case, this method may be used in a clinical setting to determine a more accurate flow rate of blood cells within vascularized tissue by eliminating the effect of camera noise on the speckle image. In a second non-limiting case, this method may be used to increase the amplitude of the pulse waveform caused by the cardiac cycle, by removing the components of the signal that arise from non-pulsatile elements.

In some embodiments, a system for determining unknown particle motion characteristics in a sample of interest using a calibrated contrast measurement from a laser speckle imaging device is disclosed. The system includes a laser speckle imaging device configured for contrast analysis, a computer-readable memory storing calibration data, and a processor operably coupled to the detector and to the computer-readable memory. The laser speckle imaging device includes a light source configured to emit light such that the light scatters within a sample and a photo-sensitive detector having one or more light-sensitive pixel elements configured to receive at least some of the scattered light. The stored calibration data comprises one or more measurements of light scattered from a calibration sample comprising light scattering particles with particle characteristics known a priori and data related to the known particle characteristics of the calibration sample and/or data derived from the combined analysis of the measurements and data. The processor is programmed to derive a contrast measurement by comparing light detected by the one or more pixels in time and/or space that has scattered from the sample of interest comprising light scattering particles with unknown particle motion characteristics. The processor is further programmed to read the stored calibration data from the computer-readable memory and calibrate the contrast measurement from the sample of interest by correlating the contrast measurement to the calibration data so as to determine the unknown particle motion characteristics of the sample of interest.

Correlating the contrast measurement to the calibration data may comprise evaluating a calibration function estimated from the one or more measurements from the calibration sample. Correlating the contrast measurement to the calibration data may comprise interpolation or extrapolation of the one or more measurements from the calibration sample. Correlating the contrast measurement to the calibration data may comprise at least partially correcting the contrast measurement to account for a measure of noise arising from undesired signals, the measure of noise being derived from the one or more measurements from the calibration sample. At least partially correcting the contrast measurement can comprise subtracting from the contrast measurement the measure of noise or dividing the contrast measurement by the measure of noise. The measure of noise may account for one or more of detector noise, light source coherence, statistical variance, and ambient or background light. The processor may be further programmed to store to the computer-readable memory a calibration result made from determining the unknown particle motion characteristics, to read the stored calibration result, and to calibrate subsequent measurements based on the stored calibration result.

The light scattering particles of the sample of interest may be blood cells and the unknown particle characteristics may be a measure of the flow rate of the blood cells. The one or more measurements from the calibration sample may be acquired from the same laser speckle imaging device used to detect the light scattered from the sample of interest in deriving the contrast measurement. The one or more measurements from the calibration sample may be acquired from a laser speckle imaging device distinct from that used to detect the light scattered from the sample of interest in deriving the contrast measurement. The one or more measurements from the calibration sample may include a measurement taken using incoherent light. Correlating the contrast measurement to the calibration data may comprise correcting the contrast measurement to be approximately zero for the measurement taken using incoherent light. The calibration data may include a look-up table comprising pairs of contrast measurements from the calibration sample and known flow rates of the light scattering particles of the calibration sample.

The laser speckle imaging device, the computer-readable memory, and the processor may be housed within a single device. The single device may be configured to be worn by a user to measure a sample of interest within the user. The laser speckle imaging device may be configured to measure pulsatile blood flow deriving from the cardiac cycle. The system may include the calibration sample. The calibration sample may be a fluid comprising light scattering particles, wherein the fluid is configured to be pumped at known volumetric flow rates.

In some embodiments, a system for determining unknown particle motion characteristics in a sample of interest using a calibrated contrast measurement from a laser speckle imaging device is disclosed. The system includes a laser speckle imaging device configured for contrast analysis, a computer-readable memory storing calibration data, and a processor operably coupled to the detector and to the computer-readable memory. The laser speckle imaging device includes a light source configured to emit light such that the light scatters within a sample and a photo-sensitive detector having one or more light-sensitive pixel elements configured to receive at least some of the light. The calibration data includes an a priori estimate of the effect on contrast arising from signals unrelated to particle motion characteristics of the light scattering particles in the sample of interest. The processor is programmed to derive an empirical measure of the total contrast in light detected by the one or more pixel elements in time and/or space that has scattered from the sample of interest comprising light scattering particles with unknown particle motion characteristics. The processor is further programmed to calibrate the empirical measure of total contrast by using the a priori estimate to correct for contrast elements that are unrelated to particle motion characteristics of the light scattering particles of the sample of interest and determine the unknown particle motion characteristics of the sample of interest from the calibrated empirical measure of total contrast.

The a priori estimate may be based on at least one previously recorded measurement. The at least one previously recorded measurement may have been taken using incoherent light. The at least one previously recorded measurement may have been recorded using the same laser speckle imaging device used to detect the light scattered from the sample of interest in deriving the empirical measure of the total contrast. The a priori estimate may be based at least in part on the noise characteristics of the detector. The a priori estimate may be based at least in part on ambient or background light. The a priori estimate may be based at least in part on light intensity variation not due to interference. The light scattering particles of the sample of interest may be blood cells and the unknown particle characteristics may include a measure of the flow rate of the blood cells. The empirical measure of total contrast may be a measure of pixel variance and the a priori estimate may be a measure of pixel variance. Correcting the empirical measure of total contrast may comprise subtracting or ratioing the a priori estimate of variance from the empirical measure of variance.

The laser speckle imaging device, the computer-readable memory, and the processor may be housed within a single device. The single device may be configured to be worn by a user to measure a sample of interest within the user. The laser speckle imaging device may be configured to measure pulsatile blood flow deriving from the cardiac cycle.

In some embodiments, a method for determining unknown particle motion characteristics in a sample of interest using a calibrated contrast measurement from a laser speckle imaging device is disclosed. The method comprises employing a laser speckle imaging device configured for contrast analysis to obtain a measurement of light scattered from a sample of interest comprising light scattering particles with unknown particle motion characteristics. The laser speckle imaging device includes a light source configured to emit light such that the light scatters within a sample and a photo-sensitive detector having one or more light-sensitive pixel elements configured to receive at least some of the scattered light. The method further comprises accessing calibration data from a computer-readable memory. The calibration data includes one or more measurements of light scattered from a calibration sample comprising light scattering particles with particle characteristics known a priori and data related to the known particle characteristics of the calibration sample and/or data derived from the combined analysis of the one or more measurements and the data. The method further comprises deriving a contrast measurement by comparing light detected by the one or more pixels in time and/or space from the measurement of light and calibrating the contrast measurement from the sample of interest by correlating the contrast measurement to the calibration data so as to determine the unknown particle motion characteristics of the sample of interest.

The method may further comprise employing the laser speckle imaging device to obtain the one or more measurements from the calibration sample. The calibration sample may be a fluid comprising light scattering particles with particle characteristics known a priori and the method may further comprising pumping the fluid at a known flow rate. Pumping the fluid at a known flow rate may comprise pumping the fluid at two or more different known flow rates.

The calibration sample may be a living subject, and the method may further comprise occluding blood flow within an extremity of the subject to reduce or cause a cessation of blood flow. Occluding blood flow may comprise applying a blood-pressure cuff to the ankle, legs, or arms of the subject.

The method may further comprise illuminating the calibration sample with incoherent light to obtain the one or more measurements from the calibration sample. The method may further comprise storing a result from the calibration to the computer readable memory; employing the laser speckle imaging device to obtain a subsequent measurement of light scattered from the same or a different sample of interest comprising light scattering particles with unknown particle motion characteristics; accessing the calibration result from the computer-readable memory; deriving a subsequent contrast measurement by comparing light detected by the one or more pixels in time and/or space from the subsequent measurement of light; and calibrating the subsequent contrast measurement by correlating the subsequent contrast measurement to the calibration result so as to determine the unknown particle motion characteristics. The light scattering particles of the sample of interest may be blood cells and determining the unknown particle characteristics may comprise determining the flow rate of the blood cells.

In some embodiments, a method for determining unknown particle motion characteristics in a sample of interest using a calibrated contrast measurement from a laser speckle imaging device is disclosed. The method may comprise employing a laser speckle imaging device configured for contrast analysis comprising to obtain a measurement of light scattered from a sample of interest comprising light scattering particles with unknown particle motion characteristics. The laser speckle imaging device includes a light source configured to emit light such that the light scatters within a sample and a photo-sensitive detector having one or more light-sensitive pixel elements configured to receive at least some of the scattered light. The method further comprises accessing from computer-readable memory an a priori estimate of the effect on contrast arising from signals unrelated to particle motion characteristics of the light scattering particles of the sample of interest. The method further comprises deriving an empirical measure of the total contrast in light detected by the one or more pixel elements in time and/or space from the measurement of light. The method further comprises calibrating the empirical measure of total contrast by using the a priori estimate to correct for contrast elements that are unrelated to particle motion characteristics of the light scattering particles of the sample of interest and determining the unknown particle motion characteristics of the sample of interest from the calibrated empirical measure of total contrast.

The method may further comprise employing the laser speckle imaging device to obtain the a priori estimate. Employing the laser speckle imaging device to obtain the a priori estimate may comprise pumping fluid comprising light scattering particles with particle characteristics known a priori at a known flow rate and measuring light scattered from the light scattering particles with particle characteristics known a priori. Pumping the fluid at a known flow rate may comprise pumping the fluid at two or more different known flow rates. Employing the laser speckle imaging device to obtain the a priori estimate may comprise occluding blood flow within an extremity of a living subject to reduce or cause a cessation of blood flow and measuring light scattered from the occluded extremity of the subject. Occluding blood flow may comprise applying a blood-pressure cuff to the ankle, legs, or arms of the subject.

The method may further comprise illuminating a calibration sample with incoherent light to obtain the a priori estimate. The method may further comprise employing the laser speckle imaging device to obtain a subsequent measurement of light scattered from the same or a different sample of interest comprising light scattering particles with unknown particle motion characteristics; accessing the a priori estimate from the computer-readable memory; deriving a subsequent empirical measure of the total contrast in light detected by the one or more pixel elements in time and/or space from the subsequent measurement of light; calibrating the subsequent empirical measure of total contrast by using the a priori estimate to correct for contrast elements that are unrelated to particle motion characteristics of the light scattering particles; and determining the unknown particle motion characteristics from the calibrated subsequent empirical measure of total contrast. The light scattering particles of the sample of interest maybe blood cells and determining the unknown particle characteristics may comprise determining the flow rate of the blood cells.

BRIEF DESCRIPTION OF THE DRAWINGS

These and other features, aspects, and advantages of the present disclosure will now be described with reference to the drawings of embodiments, which embodiments are intended to illustrate and not to limit the disclosure. One of ordinary skill in the art would readily appreciate that the features depicted in the illustrative embodiments are capable of combination in manners that are not explicitly depicted, but are both envisioned and disclosed herein.

FIG. 1A shows the system in a reflectance, non-contact configuration. FIG. 1B shows the system in a transmission, non-contact configuration. FIG. 1C shows the system in a reflectance, contact configuration. FIG. 1D shows the system in a transmission, contact configuration.

FIG. 2A schematically illustrates use of the interrogation device to transilluminate a subject's digit. FIG. 2B illustrates the interrogation device coupled to an external processor with display.

DETAILED DESCRIPTION

The systems, devices, and methods disclosed herein may incorporate component devices, including a light source 100, a photodetector 200 (i.e. a photosensitive detector, such as an image sensor), memory, and one or more processors, which may be operatively connected to one another to interrogate a sample 300. In many embodiments, the sample may be a physiological sample, such as a region of tissue on a subject, about which physiological information is to be ascertained. The subject may be a living animal, such as a human. The component devices may be standard devices employed in new configurations, methodologies, and/or systems or they may be devices specifically designed or adapted to perform in the systems and methods disclosed herein. The light source 100 may be configured to emit at least partially coherent light. The light source 100 may be a laser, such as a diode laser. In some embodiments, the light source 100 is a VCSEL laser. The photodetector 200 may comprise one or more light-sensitive elements (e.g., pixels) for detecting light recovered from the light source 100 after interaction with a sample. The photodetector 200 may, for example, be a silicon-based camera sensor. The camera sensor may be of any suitable type, including but not limited to CMOS or CCD image sensors. The photodetector 200 may be configured to generate one or more signals related to the detected light and to transmit these signals to the processor. The signals may comprise quantifiable information about the intensity of light detected at one or more pixels at a point in time or over a course of time. In some embodiments, the signals may comprise information about the wavelength(s) of the detected light. The signals may be analog or digital. If the signals are analog they may be subsequently converted into digital signals either before or after being transmitted from the photodetector 200.

Figure 1A:
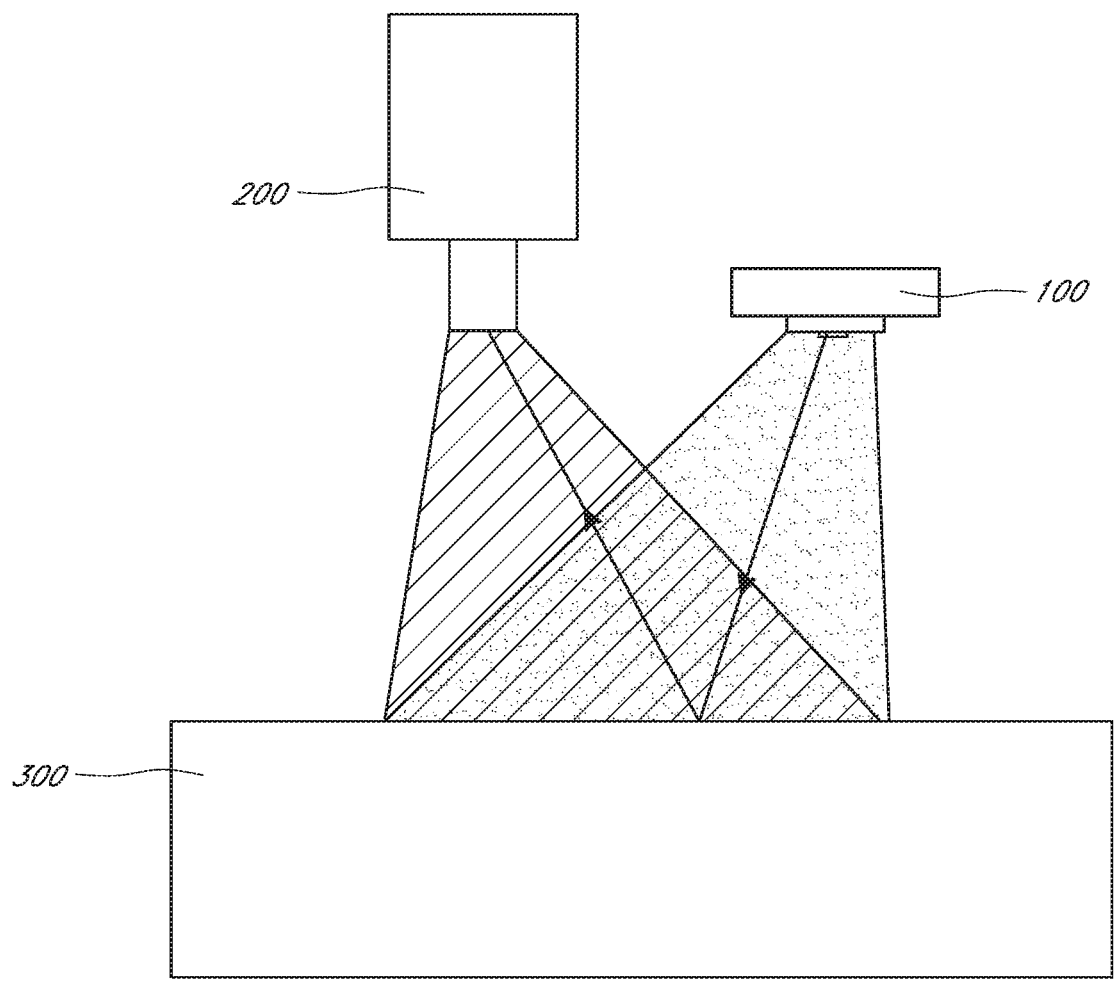
FIGS. 1A-1D schematically illustrate various system configurations.
Figure 1B:
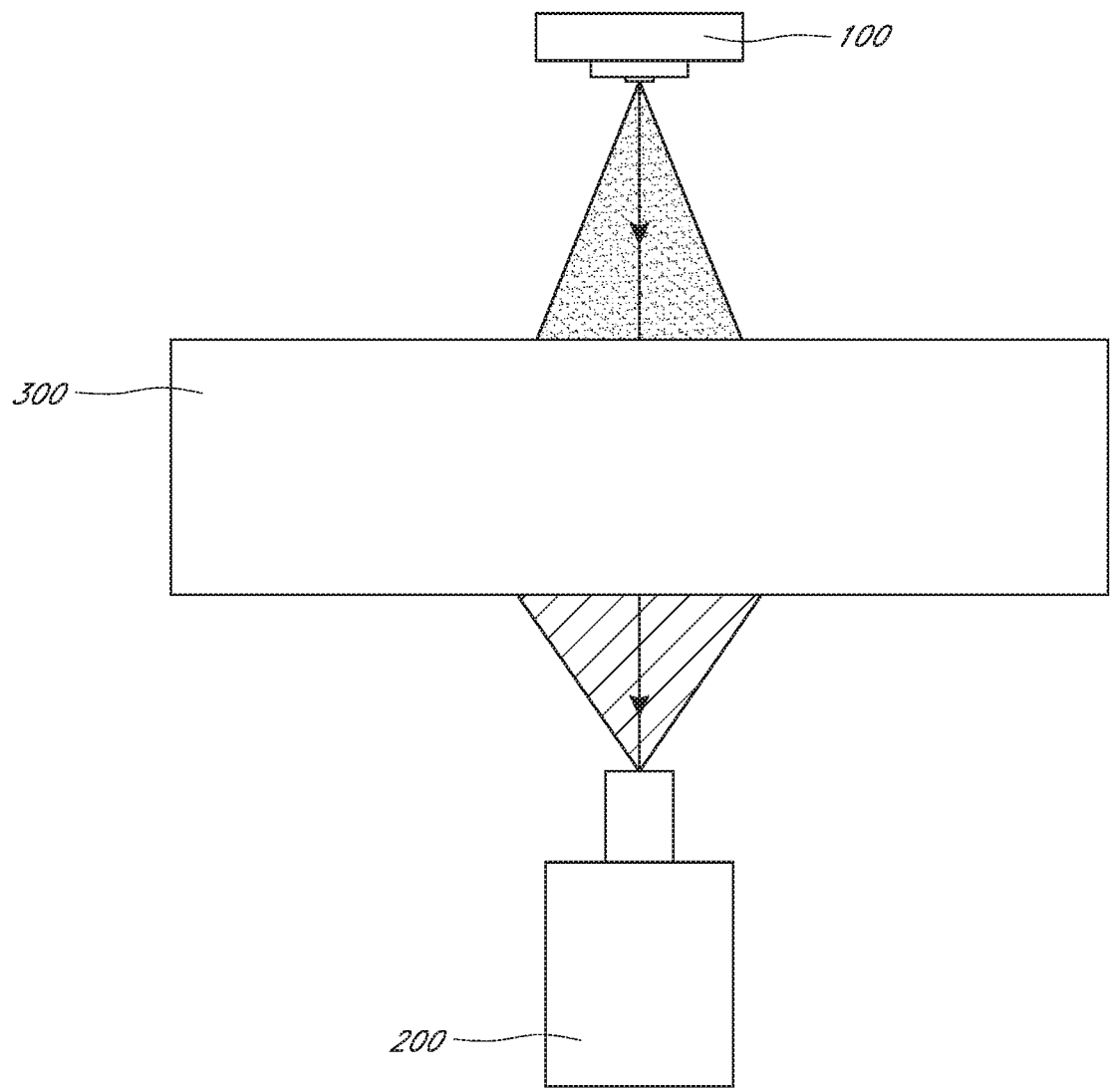
Figure 1C:
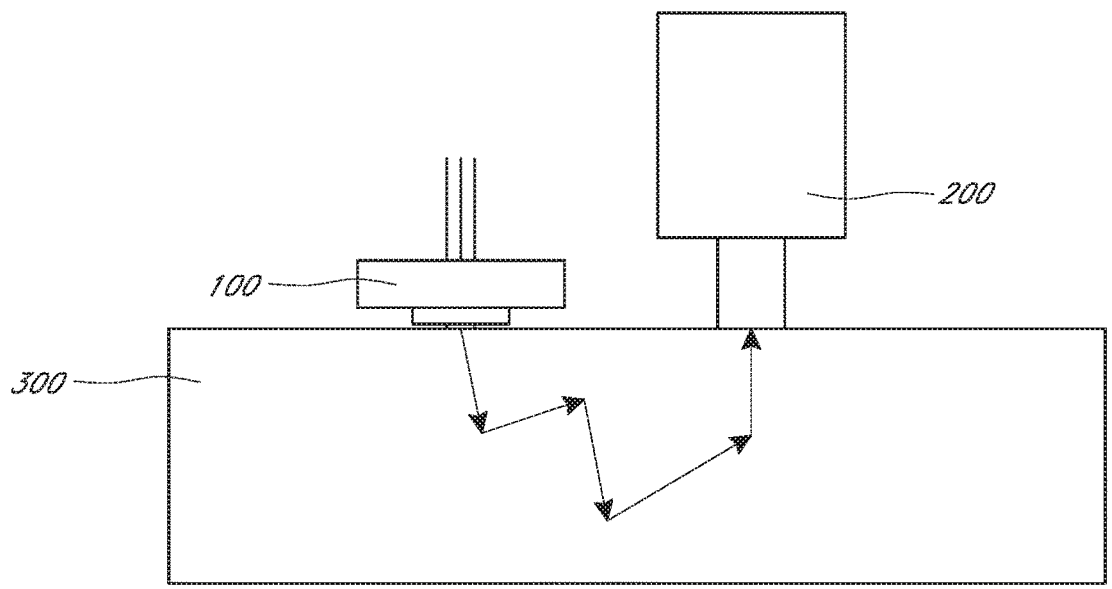
Figure 1D:
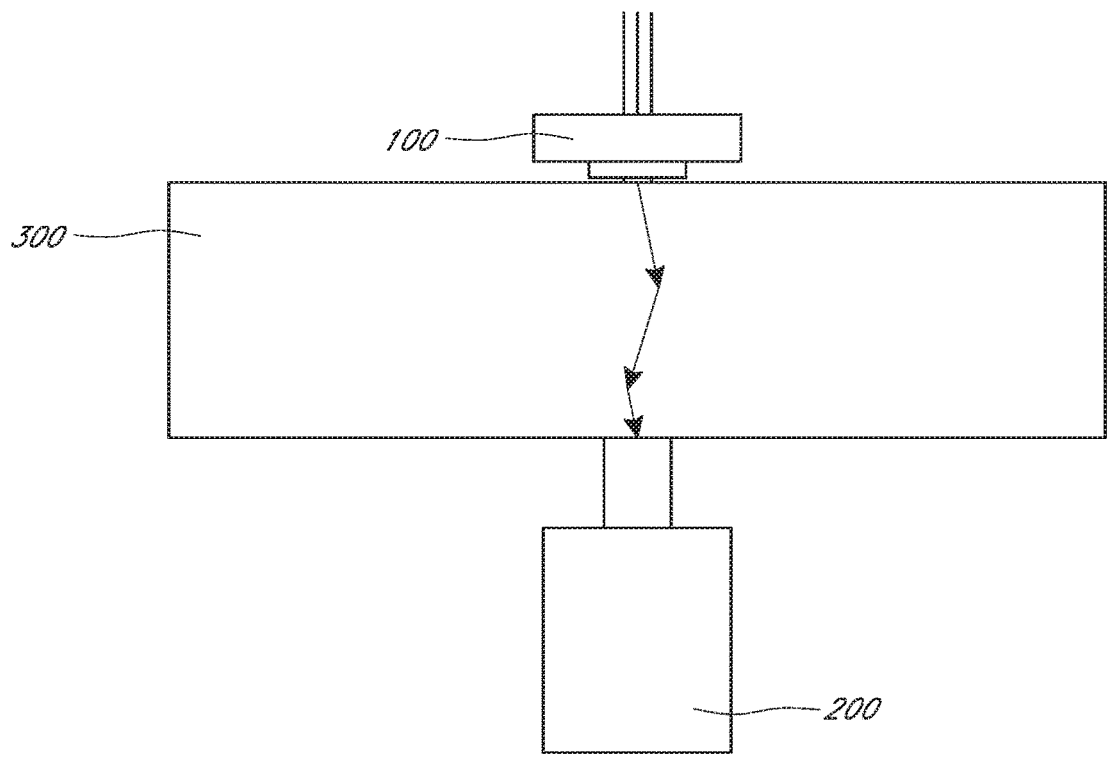

The light source 100 and photodetector 200 may be positionable in any number of configurations relative to the sample 300 including but not limited to being placed in contact or noncontact geometries, or in reflectance or transmission geometries, as seen in FIGS. 1A-1D. The devices are positionable in that they can each be maintained in a relatively constant spatial orientation relative to the sample 300 during the measurement so that changes in the detected signal resulting from movement of the light source 100, photodetector 200, and/or sample 300 relative to one another are negligible relative to the informational content attained from the sample 300. The positionable devices may be affixed to each other, part of an integral device, or distinct structures. One or both of the devices may be removably attached to the sample, such as affixed to a surface of the sample, or they may be free-standing or affixed to a structure independent of the sample 300. At least a portion of the light emitted from a positionable light source 100 is able to reach a surface of the sample 300 and at least a portion of the light detected by a positionable photodetector 200 has contacted the sample 300. FIG. 1A shows a non-contact reflectance geometry wherein the light source 100 and photodetector 200 are both positioned on the same side of the sample 300, neither of which is in direct physical contact with a surface of the sample 300. The photodetector 200 is configured to receive light reflected from the surface of the sample 300 as well as light scattered internally within the sample. FIG. 1B shows a non-contact transmission geometry wherein the light source 100 and the photodetector 200 are positioned on opposite sides of the sample 300 through which the light emitted from the light source 100 passes through and in which neither the light source 100 nor the photodetector 200 are in direct physical contact with a surface of the sample 300. The light source 100 and photodetector 200 may or may not be positioned directly across from each other in a transmission geometry. FIG. 1C shows a contact reflectance geometry wherein the light source 100 and the photodetector 200 are both positioned on the same side of the sample 300, both of which are in direct physical contact with a surface of the sample 300. FIG. 1D shows a contact transmission geometry wherein the light source 100 and photodetector 200 are positioned on opposite sides of the sample 300 through which the light emitted from the light source 100 passes through and in which both the light source 100 and the photodetector 200 are in direct physical contact with a surface of the sample 300. Variations are also possible for each geometry wherein one of the light source 100 and the photodetector 200 is in direct physical contact with a surface of the sample 300 and the other is not. These geometries as described and illustrated in FIGS. 1A-1D are non-limiting examples and the systems and methods disclosed herein may be practiced with any suitable configuration of the system components. For example, the photodetector 200 may be positioned in a configuration that neither receives surface-reflected light nor transmitted light.

In many embodiments, coherent light or at least partially coherent light is emitted by the light source 100 and directed toward the sample 300. The photodetector 200 is positioned to recover at least some of the light emitted by the light source 100 after it has interacted with the sample 300. In various embodiments, the device, system, or method may be configured to maximize collection of light scattered from light scattering particles within the sample 300, particularly light scattered from light scattering particles undergoing flow (e.g., blood cells) or other types of motion (e.g., diffusion). The light emitted by the light source 100 may be emitted at a constant intensity over a time sufficient for detection. In other embodiments, the light may be emitted according to dynamic patterns. In many embodiments, the light may be emitted and detected over a period of time sufficient to detect changes which occur in the sample 300 and which alter the path of the emitted light and/or properties of the detected light. For example, by recording over sufficient time frames, dynamic properties of light scattering particles, such as a rate of motion (e.g., flow rate) can be observed. The processor may be used to record the signal(s) detected by the photodetector 200 over time to memory and/or analyze the signals and/or the temporal changes in the signals over time to determine information about the sample 300, such as unknown particle motion characteristics of light scattering particles in the sample 300.

Figure 2A:
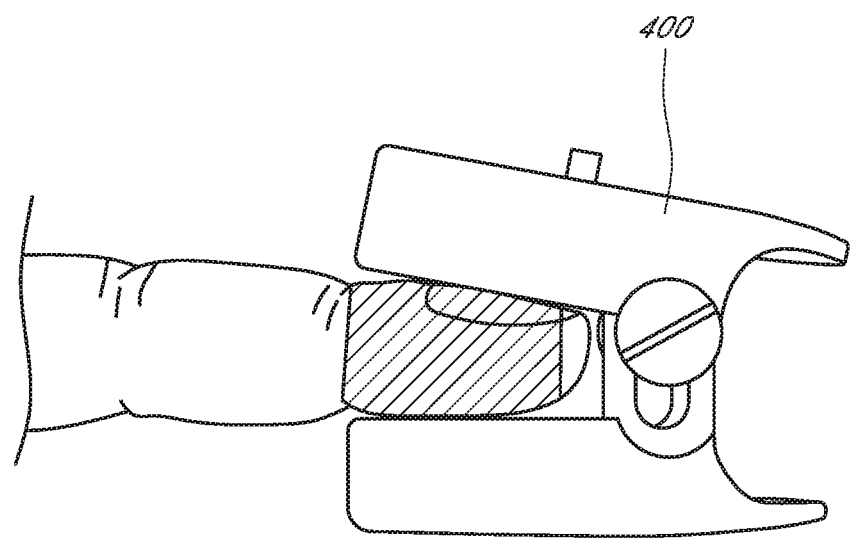
FIGS. 2A-2B illustrates an example of an interrogation device.
Figure 2B:
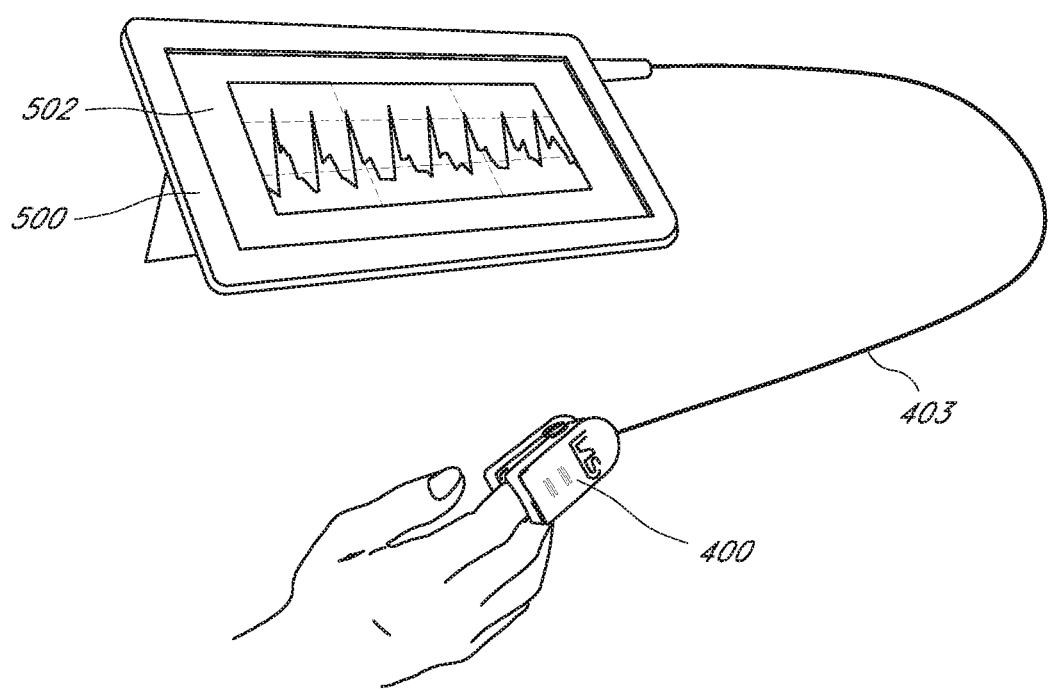

FIGS. 2A and 2B illustrate examples of an interrogation device 400, which is configured as a finger clip to interrogate blood flow within vascularized tissue of a digit (e.g., finger). FIG. 2A schematically illustrates the transillumination of a portion of the finger coupled to the interrogation device 400. FIG. 2B illustrates the interrogation device operatively coupled to an external processor 500. The interrogation device 400 can include the light source 100 and photodetector 200 in an integrated or joinable housing, as shown in FIGS. 2A and 2B. The finger clip 400 may be configured to operate in any configuration (e.g., transmission or reflectance as well as contact or non-contact). Some embodiments of the interrogation device 400 may be configured to be wearable or attachable to a subject. These may include, but are not limited to, belts, wrist-bands, skin patches, ear-clips, etc. The interrogation device 400 may be operatively coupled to the processor 500 by a data cable 402, which may transfer data and/or power between the interrogation device 400 and the processor 500. The data cable 402 may be a USB cable or any other suitable cable. In some embodiments, the interrogation device 400 may include wireless functionality for operatively coupling to the processor 500. The processor 500 can include a display 502 for displaying data, such as a detected waveform, an image of a spectral pattern, a histogram of data, etc.

Figure 3:
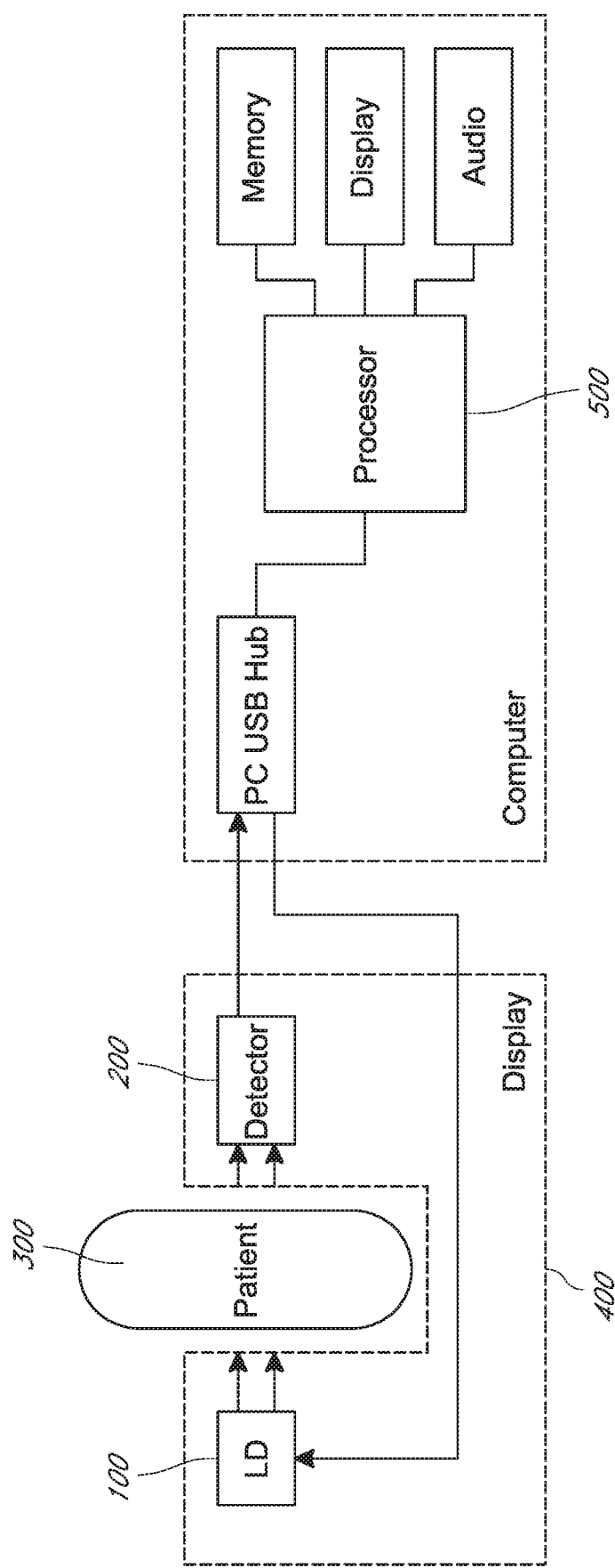
FIG. 3 schematically illustrates the components of an example system including an interrogation device coupled to a computer comprising a processor and memory.

FIG. 3 schematically illustrates the interaction of the components of an example interrogation device 400 and a computer. The processor 500 can be part of a computer, a tablet, or any other suitable device. The computer may further include a memory, a display, audio devices, and/or other components. The computer may comprise a PC USB hub for operatively coupling to the interrogation device 400. In some embodiments, a display 502 may be separate from the processor 500. In some embodiments, the interrogation device 400 can include a display. The interrogation device 400 can include the light source 100 (e.g., a laser diode) and/or the photodetector 200. In the example shown in FIG. 3, the light source 100 and the photodetector 200 are configured in a transmission geometry around a sample 300 of physiological tissue. The processor 500 may receive information from the photodetector 200, such as receive generated signals, and from the light source 100, and send instructions for controlling operation of the light source 100 and the photodetector 200. In some embodiments, the systems may incorporate feedback for modulating the emission of light from the light source 100 and/or the detection of light by the photodetector 200 according to an analysis of the detected light and/or generated signals by the processor 500.

The processor 500 may be operatively coupled to memory, which may be comprised of one or more memory components. The memory may be integral with the processor (e.g., part of an integrated chip) and/or may be external to the processor 500. The processor 500 may be configured to read and/or write to memory. For example, the processor 500 may be configured to store raw input from the photodetector 200 to the memory (e.g., raw measurements of light intensity, time points, pixel identifications) and/or may store processed or partially processed input to the memory (e.g., calculations of contrast or a metric derived therefrom, waveforms formed by the light intensity measurements, etc.). The processor 500 may be configured to read from the memory. For example, the processor 500 may read raw input from the photodetector 200 stored in the memory or partially processed input and perform further operations on the data (e.g., calculation of a volumetric flow rate from a metric of contrast, calibration of a measurement, etc.). Data stored in the memory may be stored short-term or long-term. For example, the processor 500 may send and retrieve input data to and from the memory while simultaneously performing operations on input from the photodetector 200 as the input is being generated and/or transmitted to the processor 500. The processor 500 may store data, measurements, calculations, and the like, from previous measurements/uses of the interrogation device 400 or store data from another interrogation device to be used in the processing of subsequent input from the interrogation device 400 (e.g., for calibration, as described elsewhere herein). The data stored in the memory may be written to the memory by the processor 500 or another processor operatively coupled to the memory. The stored data may be generated from the interrogation device 400, generated by another interrogation device 400, or generated by other means (e.g., input by a user into a computer or input into an interrogation device 400).

In some embodiments, the processor(s) and/or memory used in determining particle characteristics, including for example calibrating measurements derived from photodetector 200 input, may be integrated into the interrogation device 400. In some implementations, the interrogation device 400 may store measurements from previous interrogations. For example, measurements made on one or more calibration samples including light scattering particles with known particle characteristics, as described elsewhere herein, may be stored locally within the interrogation device 400 and used by the processor(s) for calibrating subsequent measurements of samples with unknown particle characteristics. Similarly, data relating to components of the interrogation device 400, such as estimates of sensor noise or light source coherence length, may be stored locally on the interrogation device 400 and used by the processor for calibrating measurements. In some embodiments, the system may comprise a pre-calibrated device without the need to interface with an external processor or memory. The calibration may be performed as part of the manufacturing process or may be subsequently calibrated. The systems and methods disclosed herein can be practiced according to any combination of processor(s) and memory. The processor and memory may be both integrated into the interrogation device 400 (i.e. internal) or both external to the interrogation device 400. The memory may be internal and the processor external or vice-versa. In some implementations, the calibrations disclosed herein may be performed using both internal and external processors and/or using internal and external memory.

The disclosed devices, systems, and methods employ an innovative concept of reducing the susceptibility of speckle images to noise and deleterious speckle pattern formulation effects by calibrating the sensor output. In some embodiments, the output may be calibrated by performing measurements of samples comprising light scattering particles with particle characteristics known a priori (e.g., known motion and/or light intensity variance). Correlating future measurements from samples with unknown particle motion characteristics to these measurements from calibration samples in combination with data related to the a priori known particle characteristics, or to data derived from a combined analysis of the measurements and known particle characteristics (e.g. a calibration function or model), may be used to correct for unwanted signals in the measurements and inform the samples of interest. The correction in subsequent contrast measurements can be used to more accurately determine particle motion characteristics.

Particle motion characteristics may generally be derived from measuring contrast in the disclosed systems. Particle motion characteristics may include volumetric flow rates of particles, diffusion coefficients (from which particle size and viscosity may be derived), degrees of laminarity/turbulence, hematocrit, blood perfusion in biological samples, etc. Other particle characteristics may include, for example, optical particle characteristics, such as absorption spectrum, absorption coefficients, scattering coefficients, reduced scattering coefficients, scattering anisotropy, etc. A priori knowledge of particle motion characteristics (e.g., flow rate) in a calibration sample may be used to correct measurements so that the determined particle motion characteristics of the calibration sample would match the true values known a priori. Non-motion particle characteristics (e.g., optical particle characteristics) may affect the measurement of contrast and ultimate determination of particle motion characteristics. For instance, high levels of absorption by light scattering particles within a sample may affect (e.g., increase) contrast. A priori knowledge of these characteristics may also be used to correct contrast measurements. For example, measurements of calibration samples with unknown flow rates but known optical particle characteristics, such as absorption coefficient, may be used to adjust for that optical particle characteristic in future samples of interest. For instance, a calibration sample with substantially 0% absorption could be measured at an unknown flow rate and the absorption coefficient increased a known amount, such as by adding an absorbing dye to the sample while at the same flow rate. The measured change in contrast as a result of absorption coefficient could be stored to memory and used to correct future empirical measurements of contrast for a sample of interest with unknown particle motion characteristics but a known (e.g., measurable) absorption coefficient.

In some embodiments, the output may be calibrated by determining an a priori estimate for the amount of unwanted signal affecting total measured contrast, which may or may not be based on prior LSI measurements, and correcting empirical measurements in samples of interest by accounting for the estimated unwanted effect on contrast. In some implementations, the correction may comprise a simple mathematical operation, such as a subtraction/addition or multiplication/division. The correction may, in a non-limiting example, take the form of simple division or subtraction of the signal derived from a relatively motionless element or object. In one embodiment, the amount of dark current in the sensor pixels could be estimated a priori based on a manufacturer specification. The estimate of the dark current could then be referenced to predict the undesired effect on pixel intensity variance and/or mean intensity, and finally subtracted from the empirical contrast calculation to estimate the noise-free contrast. In some embodiments, contrast measured from a static calibration sample arising from undesired signals may be subtracted from future measurements. For example, the contrast for a static object exhibiting no flow, such as a piece of paper, may be assumed to have a theoretical contrast of 1 when the actual measured contrast is less than 1. Any deviation from the expected result may be assumed to arise from imperfections in the system components (e.g., finite laser coherence or polarization, pixel size, sensor non-linearity, system optics, etc.). All future measurements could be divided by the calibration value (e.g., 0.8) to correct for the error. The correction may, in another non-limiting example, take the form of creating a corrective lookup-table or analytical calibration function.

Disclosed herein are novel methods, systems, and devices for the calibration of speckle contrast flowmetry measurements using previously recorded data from samples at a known volumetric flow or known or expected contrast. Broadly, the disclosure relates to an innovative method to calibrate a dynamic light scattering measurement, and in particular the speckle contrast analysis method. The LSI devices disclosed herein are configured to measure the optical contrast detected by the one or more pixels of the photodetector and may be referred to as laser speckle contrast analysis devices. Advantageously, the images detected by the photodetector 200 of the present disclosure can be unfocused. The rate of motion (e.g., flow rate) can be determined from a global average of the detected speckle contrast rather than by mapping the detected speckle pattern to focused light scattering particles. Configuring the photodetector 200 to obtain focused images can be expensive and spatially constraining. Photodetectors 200 configured to accept unfocused light may advantageously be smaller and may be more suitable to be worn by a user. As such, the photodetector 200 may be configured to accept unfocused (i.e. non-convergent) light rays. For example, the photodetector 200 may be configured to accept raw unaltered light paths that have not been altered by optical elements, such as a lens, which modify the path or direction of the impinging light.

The method of speckle contrast imaging is commonly used to image vessels and vascularized tissues within the field of biomedical engineering and medicine [7]. The method takes advantage of the interference pattern formed when coherent laser light scatters randomly in a sample media. The so-called speckle pattern is formed onto an image sensor. If the scattering objects are in motion, the speckle pattern will fluctuate during the exposure time of the image sensor, which will cause a blurring of the pattern. For a given camera exposure, faster fluctuations induce more blurring. One measure of the "blur" in a speckle image is commonly referred to as the speckle contrast, and is conventionally defined as:

$$K=\sigma/\langle I \rangle \quad [1]$$

where $\sigma$ is the standard deviation and $\langle I \rangle$ is the mean of N pixel intensities (for a silicon-based image sensor, the pixel intensity is proportional to the voltage output from the detector element). Other measures of contrast can be used as well, with contrast being defined generally as any measure of disparity, difference, or distinction between values of multiple pixel elements of the photodetector 200, and/or the evolution of a single pixel element over time. Non-limiting examples include statistical properties of the spatial or temporal contrast, such as the speckle flow index (defined as $k_0/K^2$ where K is the speckle contrast as described herein and $k_0$ is a constant), standard deviation from mean or median, difference metrics such as mean percent difference (e.g., between pixels of the photodetector 200), potential-well fill time difference, gradient between pixels, metrics of comparisons between subregions such as subtraction, the magnitude of fluctuation in the pixel intensities over time, reduction of the pixels to local binary patterns or local ternary patterns, etc. An autocorrelation performed on the signal generated by a single pixel over a period of time may quantify the temporal decorrelation in detected light intensity as a result of the motion of the moving light scattering particles.

As a non-limiting example of relating a metric of contrast to the flow rate of moving particles, the spatial speckle contrast can be related to the autocorrelation time of the speckle image, which can then be related to the mean square displacement (e.g. flow speed or diffusion) of the moving scattering objects [6]. In general, a relatively high contrast speckle pattern will produce higher values of K and a more blurry pattern will produce lower values of K. The rate of movement (e.g., flow) within a sample can then be related to the contrast, which can be computed either through analytic or empirical means. It should also be noted that temporal calculations of K, where contrast is derived from a single optical detection element over time can be used interchangeably with spatial computations of contrast. Temporal calculations of K depend on the arithmetic comparison of different intensity values within a single optical element over a period of time. In this case, multiple values for a single optical element collected over a sequence of time are compared to one another, as opposed to the comparison of values of an optical detection element to that of its surrounding neighbors at the same moment in time. While temporal calculations of K involve the comparison of a single optical element to itself, by comparing different values detected over time, the ultimate calculation of K can and often involves multiple optical detection elements. Additionally, combinations of spatial and temporal calculations of contrast may also be used without a loss of generality. In some embodiments, the rate of movement may be determined as the speed, or average speed (e.g., m/s), of the moving light scatterers within a sample. The flow rate may be a measure of the volume of fluid (e.g., blood) transported per unit of time (i.e. volumetric flow) and may be represented in any suitable units (e.g., cm$^3$/s). In some embodiments, the flow rate may be determined as a measure of volumetric flux (e.g., m$^3 \cdot$s$^{-1} \cdot$m$^{-2}$) through, for example, a blood vessel or blood vessels.

Figure 4:
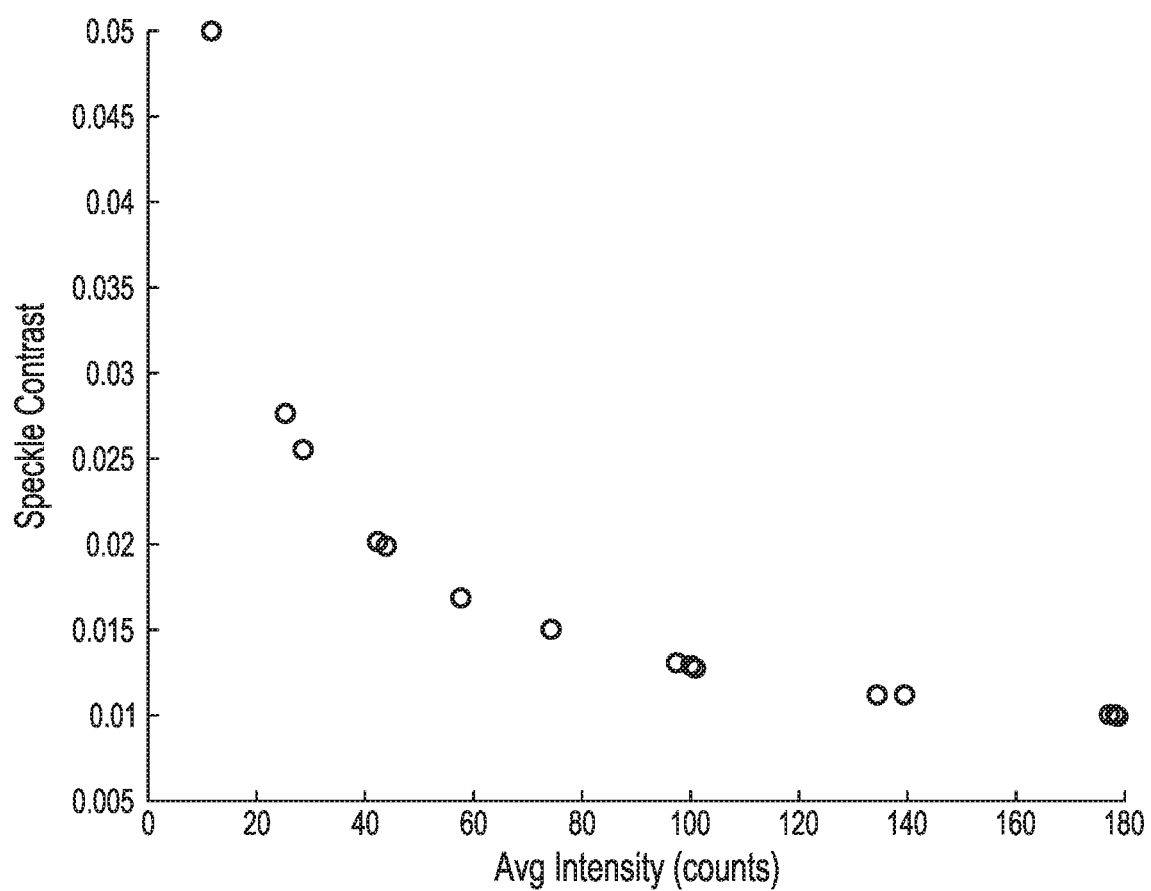
FIG. 4 illustrates an example of expected contrast error measured for a photodetector illuminated by different intensities of incoherent light.

The present disclosure relates to novel devices, systems, and methods for calibrating and/or correcting the speckle contrast, in a manner that accounts for detector noise and/or other non-flow factors that may cause undesired errors in a measurement. In some embodiments, the calibration step involves measurement of known or expected contrast. The measurement of known or expected contrast may be used to correct subsequent measurements of unknown contrast, prior to determining unknown particle characteristics in a sample of interest. For example, the expected contrast during illumination under incoherent light is 0. If the contrast measurement of a speckle flowmetry system is not 0 in these conditions, the contrast may be corrected to achieve the expected result of 0. FIG. 4 illustrates an example of a measured speckle flow metric, the speckle contrast K as defined by eq. 1, averaged across the photodetector 200, illuminated by incoherent light. The measured contrast is expected to be 0 at all intensities of light, yet is non-zero at all measured intensities. The measured contrast drastically increases as the intensity of light is reduced. The nonzero speckle contrast can be due to camera noise effects, which vary as a function of intensity. To correct for this error in the measure of contrast, the values plotted here for each intensity can be subtracted from future contrast measurements as a process of calibration to account for camera noise.

In a non-limiting case, the detector noise and other non-flow elements may be assumed to be an additive term to the variance, $\sigma^2$, between pixels, and is described as:

$$\sigma^2_{measure} = \sigma^2_{true} + \sigma^2_{noise}. \quad [2]$$

Under illumination of incoherent light, as described in the example above, $\sigma_{true}$ is presumed to be 0. Thus, $\sigma_{noise}$ can be solved for algebraically. The term $\sigma_{noise}$ may be assumed to be constant noise from factors such as camera current, shot noise, ambient light, etc. Thus, $\sigma_{noise}$ may be subtracted from future measurements to eliminate effects from noise parameters and determine $\sigma_{true}$. The value of $\sigma_{true}$, can then be used further to determine a metric of calibrated contrast by using, for example, the conventional contrast in eq. 1. Some embodiments can comprise other ways to determine or estimate $\sigma_{noise}$. These may be, but are not limited to, a priori estimates from the specifications of the sensor pixels or coherent source, through expected stochastic process statistics, through measurement of background light by a different sensor, or by assuming equivalent performance as other systems (e.g., interrogation devices) already measured.

In some embodiments, the calibration step involves the measurement of contrast for a sample with a known particle characteristic (e.g., flow rate). In one non-limiting example, a sample of light scattering fluid (a fluid comprising light scattering particles) may be pumped at a known volumetric flow rate through a tube, channel, or other container. A portion or the entirety of the tube, channel, or container may be transparent to optimize interrogation of the fluid with light. The sample may then be illuminated by coherent light, and the contrast values of the detection system recorded for varying rates of flow. Unknown particle motion characteristics from new samples of interest may then be determined by comparing the measured contrast to that measured for the sample with known flow.

A calibration function can be determined using contrast measurements derived from known volumetric flow rates. One may assume the contrast can be related to the volumetric flow through an unknown function:

$$\text{Flow} = f(K). \quad [3]$$

The speckle contrast, K, or any other suitable measure of contrast may be employed by the function. The term f(K) may be assumed to be an unknown function, which may be approximated through simulation, analytic modeling work, or left unknown. Through measurements of known flow, f(K) may be determined empirically. In a non-limiting case, the function may be assumed to be continuous, and a table of Flow vs. K pairs may be created, wherein future measurements of K may be interpolated or extrapolated between known pairs. For example, a data-set may be stored to memory comprising a look-up table. The look-up table can include pairs of measurements and known particle characteristics. For instance, each pair may include a measure of contrast generated by interrogating a sample with known particle characteristics and the associated known particle characteristic (e.g., value of the flow rate or absorption coefficient). The look-up table may, for example, include, a range of known flow rates of fluid comprising light scattering particles pumped through a calibration sample, the flow rates being selected across a continuous range of flow, and the respective measures of contrast derived from the photodetector 200 input as measured from the calibration sample for each known flow rate. The processor may then use the look-up table to interpolate the unknown particle characteristic (e.g., flow rate) of a measured sample of interest by comparing the empirically measured contrast to the stored measures of contrast in the look-up table. The processor may assume the true particle characteristic of the sample of interest lies between values of the stored particle characteristics corresponding to the measures of contrast immediately greater than and immediately less than the measured contrast of the unknown sample. In some implementations, the processor may assume a linear relationship between the measure of contrast and the particle characteristic between immediately adjacent stored data pairs.

In a second non-limiting case, f(K) may be determined through neural networks, where future measurements of K may be fed into the forward network, which then outputs a best approximation of the Flow metric. Calibration measurements of K for known flow rates may be used to train the neural network. Using larger numbers of calibration measurements may result in a more accurate neural network.

In a third non-limiting case, f(K) may be approximated through simulation or analytic modeling work, and any unknown parameters within the model may be estimated or solved for by comparing the Flow vs. K pairs. Simulations may rely on random number generators and assumed probability distributions to approximate the contrast for particles of known flow rates. For example, a Monte Carlo simulation can be used simulate the path of many photons, including scattering angles and length between scattering events, to statistically calculate the measure of contrast across multiple flow rates. Interpolation may be used to accurately determine unknown flow rates from measured values of contrast. Analytical approximations may use some approximation of scattered photon properties (e.g., a diffusion equations) to determine a continuous closed form solution which can be evaluated for any measure of contrast. For example, an assumed particle velocity distribution (e.g., Lorenztian) may be used to estimate an autocorrelation function of the remitted light, which could be integrated over time to approximate contrast as a continuous function of velocity. The analytical model can include a variable term (e.g., a scalar multiple, exponent, additive term, etc.) to account for deviation from the predicted solution. The variable term could be determined for a given system by using an optimizer to fit the analytical model, keeping the variable term as a free term, to a set of empirically determined data from a calibration sample. The resolved variable term could be used to more accurately determine particle motion characteristics from future contrast measurements using the analytical model.

In a fourth non-limiting case, the function f(K) may be estimated by common functions, such as polynomial series, exponential function, geometric function (e.g., sine, cosine, tangent), Fourier series, Taylor series, statistical distribution (e.g., Gaussian), or other function, wherein future values of K may be inserted into the expression to yield a value of Flow. The scope of the present disclosure includes all other means for determining a relationship between f(K) and flow using previously determined measurements at known flow values.

Figure 5:
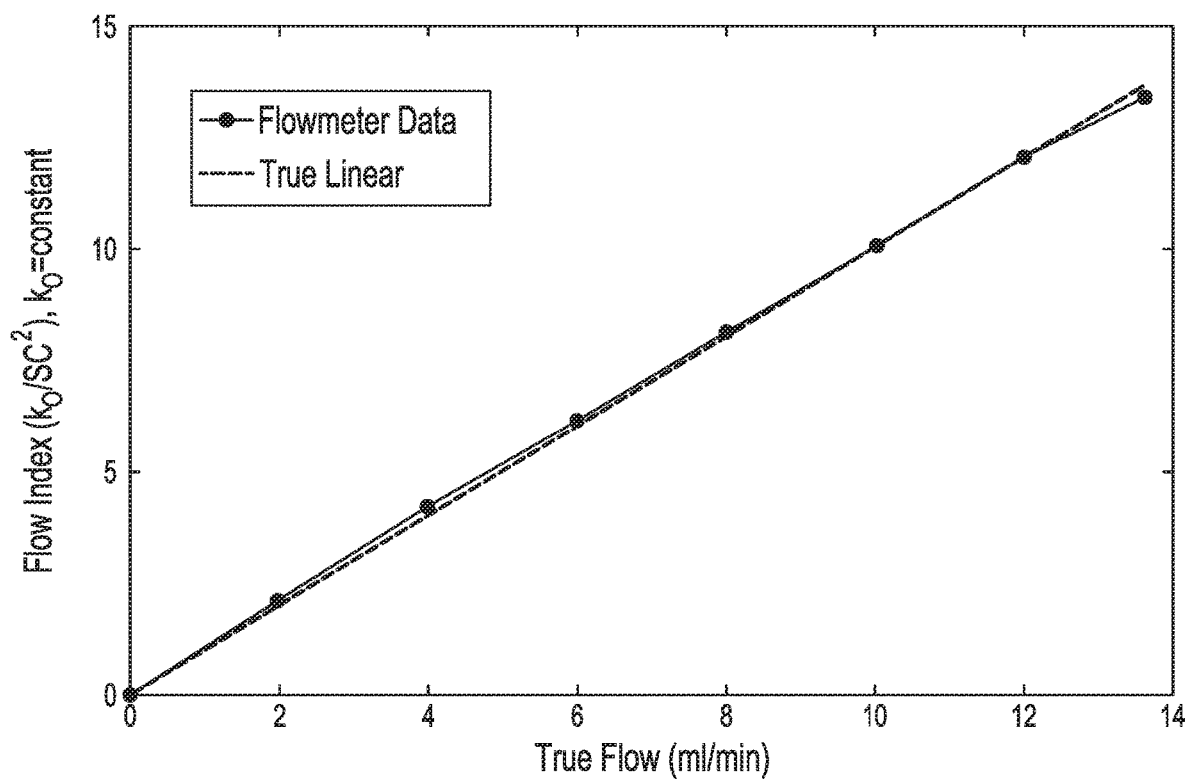
FIG. 5 illustrates an example of flow indices measured by LSI plotted against known values of the true flow rate for a calibration sample.

FIG. 5 illustrates an example of a calculated speckle flow metric, the flow index (defined elsewhere herein), averaged across the photodetector 200, as measured for a calibration sample subjected to known flow rates of light scattering particles. The flow index is approximately linear with flow. The values plotted can be used to generate a look-up table of values, where future values of flow index or K in a sample of unknown conditions can be interpolated into, as described elsewhere herein. Alternatively, the equation of the fitted line may be solved and future values of flow index or K converted to true measures of volumetric flow using the linear approximation, as described elsewhere herein.

A calibration can also be performed using physiological measurements under known or expected conditions. For example, during an occlusion of the extremities, there is a cessation or significant reduction of blood flow to the hands and/or feet. An occlusion can be carried out using a device such as, but not limited to, a blood-pressure cuff often placed over the ankle, to produce cessation of blood flow to the feet, and over the bicep to produce cessation of blood flow to the hands. After blood flow is stopped to the hands and or feet, the measured value is expected to represent a state of no flow and can be offset as such. This form of calibration can allow for customization due to subject-to-subject variability, and can be carried out independently or used in conjunction with the other aforementioned calibration methods. A physiological method of calibration can also aid in calibrating for differences between a subject's own hands and feet, for instance. Furthermore, while the examples presented above are illustrated with hands and feet, this methodology can be applied to any measurement of blood flow within the vascularized tissue.

The disclosed systems and methods may produce a more reliable device with applications in healthcare and wearable technology. For example, the system could provide more accurate measurements of flow, or provide a larger pulsatile amplitude for detecting the cardiac waveform. A system could be integrated into a wearable wrist monitor, to perform blood flow monitoring or heart rate monitoring. The blood flow and heart rate monitoring could be improved using the calibration technique described above. In a second non-limiting example, a system could miniaturized and placed on a medical device intended to monitor vascular health, where the vascular flow can be made more accurate through calibration. In this example, the medical device could be affixed to tissue of interest to clinicians and the disclosed system and method could be used to measure the flow of red blood cells within this tissue. Specifically, the medical device could, for example, be affixed to a patient's foot so that blood flow could be quantified in this tissue using the disclosed system and method. In such tissue (and others), blood circulation is required to deliver oxygen and remove cellular waste products. As such, a minimal amount of blood flow is required to sustain continued tissue viability such that nutrient delivery is adequate to meet metabolic tissue demands. The disclosed system and method could thus be used to measure blood flow (circulation) in the tissue for the purpose of determining whether the measured quantity is consistent with continued tissue viability, and as such, be used to assess the degree of blood circulation adequacy. The processor may be programmed to compare the measured blood flow (circulation) to a predetermined value and determine whether the blood circulation is adequate.

WORKING EXAMPLE

Figure 6:
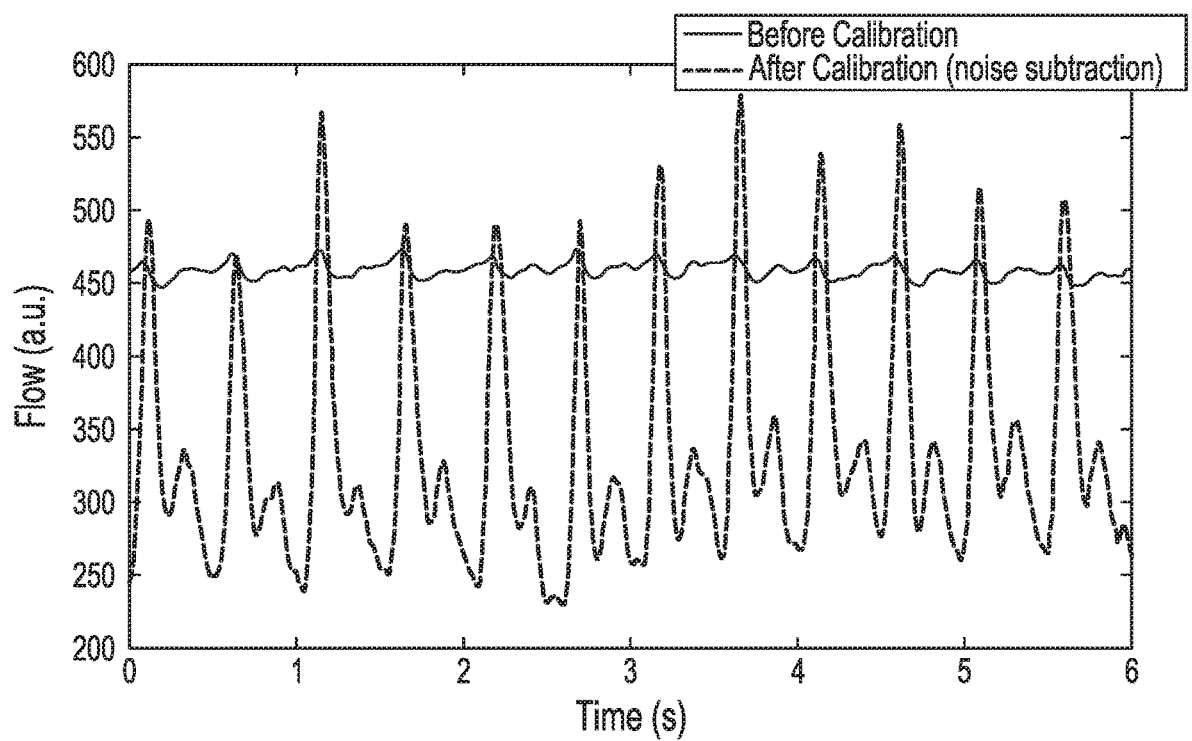
FIG. 6 illustrates a before-and-after example of using the disclosed calibration to improve the photodetector output of an LSI system used to measure the pulsatile blood flow of a subject.

FIG. 6 illustrates an example of data output from an interrogation device, such as illustrated in FIGS. 2A and 2B, and operated according to the methods and systems described herein. The measured waveforms correlate to the pulsatile blood flow originating from the cardiac cycle. The pulsatility reflects the changes in the volumetric flow rate as the subject's heart pumps blood through the interrogated vasculature. The periodicity of the flow arises from the cardiac cycle and can be used to determine heart rate by determining the period between successive waveform features (such as systolic contraction peaks). The output from the photodetector 200 is shown before accounting for noise and non-flow elements and after non-flow elements are accounted for through calibration. The calibration in this example was performed utilizing previously recorded contrast data on a calibration sample subject to static flow and interrogated under incoherent light conditions. The noise measured during calibration was subtracted from the present photodetector measurements recorded over time. As shown in FIG. 6, the calibration effectively reduced the measured non-pulsatile contrast elements, essentially amplifying the true flow signal.

While the present invention has been described in terms of particular embodiments and applications, in both summarized and detailed forms, it is not intended that these descriptions in any way limit its scope to any such embodiments and applications, and it will be understood that many substitutions, changes and variations in the described embodiments, applications and details of the method and system illustrated herein and of their operation can be made by those skilled in the art without departing from the spirit of this invention.

REFERENCES

Incorporated Herein By Reference Thereto

1. M. D. Stern and D. L. Lappe, "Method of and apparatus for measurement of blood flow using coherent light," U.S. Pat. No. 4,109,647A (1978).

2. R. Pecora, Dynamic light scattering: applications of photon correlation spectroscopy (Springer Science & Business Media, 2013).

3. A. Taniji and M. Ishikawa, "Apparatus for measuring blood flow," U.S. Pat. No. 5,291,886 (1994).

4. G. E. Nilsson and J. T. Tenland, "Method and apparatus for measuring flow motions in a fluid," U.S. Pat. No. 4,476,875A (1984).

5. J. D. Briers, "Laser Doppler, speckle and related techniques for blood perfusion mapping and imaging," Physiological measurement 22, R35 (2001).

6. J. D. Briers and S. Webster, "Laser speckle contrast analysis (LASCA): a nonscanning, full-field technique for monitoring capillary blood flow," BIOMEDO 1, 174-179 (1996).

7. D. A. Boas and A. K. Dunn, "Laser speckle contrast imaging in biomedical optics," BIOMEDO 15, 011109-011109-011112 (2010).

8. P. Zakharov, A. Völker, A. Buck, B. Weber, and F. Scheffold, "Quantitative modeling of laser speckle imaging," Opt. Lett. 31, 3465-3467 (2006).

9. S. E. Skipetrov, J. Peuser, R. Cerbino, P. Zakharov, B. Weber, and F. Scheffold, "Noise in laser speckle correlation and imaging techniques," Opt. Express 18, 14519-14534 (2010).

What is claimed is:

1. A system for determining unknown particle motion characteristics in a sample of interest using a calibrated contrast measurement from a laser speckle imaging device, the system comprising:
   a laser speckle imaging device configured for contrast analysis comprising:
      a light source configured to emit light such that the light scatters within a sample; and
      a photo-sensitive detector comprising one or more light-sensitive pixel elements configured to receive at least some of the scattered light;
   a computer-readable memory storing calibration data, the calibration data comprising:
      one or more measurements of light scattered from a calibration sample comprising light scattering particles with particle characteristics known a priori and data related to the known particle characteristics of the calibration sample;
   and/or
      data derived from the combined analysis of the one or more measurements from the calibrations sample and the data related to known particle characteristics; and
   a processor operably coupled to the detector and to the computer-readable memory, the processor being programmed to:
      derive a contrast measurement by comparing light detected by the one or more pixels in time and/or space that has scattered from the sample of interest comprising light scattering particles with unknown particle motion characteristics;
      read the stored calibration data from the computer-readable memory; and
      calibrate the contrast measurement from the sample of interest by correlating the contrast measurement to the calibration data so as to determine the unknown particle motion characteristics of the sample of interest.

2. The system of claim 1, wherein correlating the contrast measurement to the calibration data comprises evaluating a calibration function estimated from the one or more measurements from the calibration sample.

3. The system of claim 1, wherein correlating the contrast measurement to the calibration data comprises interpolation or extrapolation of the one or more measurements from the calibration sample.

4. The system of claim 1, wherein correlating the contrast measurement to the calibration data comprises at least partially correcting the contrast measurement to account for a measure of noise arising from undesired signals, the measure of noise being derived from the one or more measurements from the calibration sample.

5. The system of claim 4, wherein at least partially correcting the contrast measurement comprises subtracting from the contrast measurement the measure of noise or dividing the contrast measurement by the measure of noise.

6. The system of claim 4, wherein the measure of noise accounts for one or more of detector noise, light source coherence, statistical variance, and ambient or background light.

7. The system of claim 1, wherein the processor is further programmed to store to the computer-readable memory a calibration result made from determining the unknown particle motion characteristics, to read the stored calibration result, and to calibrate subsequent measurements based on the stored calibration result.

8. The system of claim 1, wherein the light scattering particles of the sample of interest are blood cells and the unknown particle characteristics comprise a measure of the flow rate of the blood cells.

9. The system of claim 1, wherein the one or more measurements from the calibration sample are acquired from the same laser speckle imaging device used to detect the light scattered from the sample of interest in deriving the contrast measurement.

10. The system of claim 1, wherein the one or more measurements from the calibration sample are acquired from a laser speckle imaging device distinct from that used to detect the light scattered from the sample of interest in deriving the contrast measurement.

11. The system of claim 10, wherein the one or more measurements from the calibration sample comprise a measurement taken using incoherent light.

12. The system of claim 11, wherein correlating the contrast measurement to the calibration data comprises correcting the contrast measurement to be approximately zero for the measurement taken using incoherent light.

13. The system of claim 1, the calibration data comprise a look-up table comprising pairs of contrast measurements from the calibration sample and known flow rates of the light scattering particles of the calibration sample.

14. The system of claim 1, wherein the laser speckle imaging device, the computer-readable memory, and the processor are housed within a single device.

15. The system of claim 14, wherein the single device is configured to be worn by a user to measure a sample of interest within the user.

16. The system of claim 1, wherein the laser speckle imaging device is configured to measure pulsatile blood flow deriving from the cardiac cycle.

17. The system of claim 1, further comprising the calibration sample.

18. The system of claim 1, wherein the calibration sample is a fluid comprising light scattering particles, wherein the fluid is configured to be pumped at known volumetric flow rates.

19. A method for determining unknown particle motion characteristics in a sample of interest using a calibrated contrast measurement from a laser speckle imaging device, the method comprising:
- employing a laser speckle imaging device configured for contrast analysis to obtain a measurement of light scattered from a sample of interest comprising light scattering particles with unknown particle motion characteristics, the laser speckle imaging device comprising:
  - a light source configured to emit light such that the light scatters within a sample; and
  - a photo-sensitive detector comprising one or more light-sensitive pixel elements configured to receive at least some of the scattered light;
- accessing calibration data from a computer-readable memory, the calibration data comprising:
  - one or more measurements of light scattered from a calibration sample comprising light scattering particles with particle characteristics known a priori and data related to the known particle characteristics of the calibration sample;
  - and/or
  - data derived from the combined analysis of the one or more measurements from the calibrations sample and the data related to known particle characteristics;
- deriving a contrast measurement by comparing light detected by the one or more pixels in time and/or space from the measurement of light; and
- calibrating the contrast measurement from the sample of interest by correlating the contrast measurement to the calibration data so as to determine the unknown particle motion characteristics of the sample of interest.

20. The method of claim 19, further comprising employing the laser speckle imaging device to obtain the one or more measurements from the calibration sample.

21. The method of claim 20, wherein the calibration sample is a fluid comprising light scattering particles with particle characteristics known a priori, the method further comprising pumping the fluid at a known flow rate.

22. The method of claim 21, wherein pumping the fluid at a known flow rate comprises pumping the fluid at two or more different known flow rates.

23. The method of claim 20, wherein the calibration sample comprises a living subject, the method further comprising occluding blood flow within an extremity of the subject to reduce or cause a cessation of blood flow.

24. The method of claim 23, wherein occluding blood flow comprises applying a blood-pressure cuff to the ankle, legs, or arms of the subject.

25. The method of claim 19, further comprising illuminating the calibration sample with incoherent light to obtain the one or more measurements from the calibration sample.

26. The method of claim 19, further comprising:
- storing a result from the calibration to the computer readable memory;
- employing the laser speckle imaging device to obtain a subsequent measurement of light scattered from the same or a different sample of interest comprising light scattering particles with unknown particle motion characteristics;
- accessing the calibration result from the computer-readable memory;
- deriving a subsequent contrast measurement by comparing light detected by the one or more pixels in time and/or space from the subsequent measurement of light; and
- calibrating the subsequent contrast measurement by correlating the subsequent contrast measurement to the calibration result so as to determine the unknown particle motion characteristics.

27. The method of claim 19, wherein the light scattering particles of the sample of interest are blood cells and determining the unknown particle characteristics comprises determining the flow rate of the blood cells.

* * * * *